United States Patent
Tellis et al.

(10) Patent No.: US 12,424,333 B2
(45) Date of Patent: Sep. 23, 2025

(54) AUTOMATICALLY SETTING WINDOW WIDTH/LEVEL BASED ON REFERENCED IMAGE CONTEXT IN RADIOLOGY REPORT

(71) Applicant: KONINKLIJKE PHILIPS N.V., Eindhoven (NL)

(72) Inventors: Ranjith Naveen Tellis, Cambridge, MA (US); Thusitha Dananjaya De Silva Magotuwana, Yonkers, NY (US); Yuechen Qian, Briarcliff Manor, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 691 days.

(21) Appl. No.: 15/035,929

(22) PCT Filed: Nov. 24, 2014

(86) PCT No.: PCT/IB2014/066280
§ 371 (c)(1),
(2) Date: May 11, 2016

(87) PCT Pub. No.: WO2015/079373
PCT Pub. Date: Jun. 4, 2015

(65) Prior Publication Data
US 2016/0292359 A1    Oct. 6, 2016

Related U.S. Application Data

(60) Provisional application No. 61/908,864, filed on Nov. 26, 2013.

(51) Int. Cl.
| | |
|---|---|
| G16H 50/70 | (2018.01) |
| G06F 16/2457 | (2019.01) |
| G06F 16/51 | (2019.01) |
| G06F 16/904 | (2019.01) |
| G06V 30/414 | (2022.01) |
| G16H 30/40 | (2018.01) |
| G16H 70/60 | (2018.01) |

(52) U.S. Cl.
CPC ....... *G16H 50/70* (2018.01); *G06F 16/24575* (2019.01); *G06F 16/51* (2019.01); *G06F 16/904* (2019.01); *G06V 30/414* (2022.01); *G16H 30/40* (2018.01); *G16H 70/60* (2018.01)

(58) Field of Classification Search
CPC .............................................. G06Q 50/22–26
See application file for complete search history.

(56) References Cited

U.S. PATENT DOCUMENTS 6,520,912 B1 * 2/2003 Brooks ................. A61B 8/461
                                                    600/437
8,638,997 B2    1/2014 Dirckx
(Continued)

*Primary Examiner* — Neal Sereboff

(57) ABSTRACT

A system and method for automatically setting image viewing context. The system and method perform the steps of extracting image references and body parts associated with the image references from a report, mapping each of the body parts to an image viewing context so that image references associated are also associated with the image viewing context, receiving a user selection indicating an image to be viewed, determining whether the user selection is one of the image references associated with the image viewing context and displaying the image of the user selection.

12 Claims, 3 Drawing Sheets

(56) References Cited

U.S. PATENT DOCUMENTS

| | | | |
|---|---|---|---|
| 8,837,794 B2 | 9/2014 | Nakamura | |
| 9,081,877 B2 | 7/2015 | Futami et al. | |
| 9,129,360 B2 | 9/2015 | Wiemker et al. | |
| 9,129,361 B2 | 9/2015 | Zhang et al. | |
| 9,269,059 B2 | 2/2016 | Mandyam et al. | |
| 9,307,909 B2 | 4/2016 | Hewett et al. | |
| 2003/0142328 A1* | 7/2003 | McDaniel | H04N 1/00477 358/1.9 |
| 2003/0198371 A1 | 10/2003 | Ono | |
| 2004/0170308 A1 | 9/2004 | Belykhigor et al. | |
| 2006/0111937 A1* | 5/2006 | Yarger | G16H 30/40 382/128 |
| 2006/0132508 A1* | 6/2006 | Sadikali | G06T 19/00 345/665 |
| 2007/0160271 A1 | 7/2007 | Doi et al. | |
| 2007/0286525 A1 | 12/2007 | Mahesh et al. | |
| 2007/0286725 A1 | 12/2007 | Su | |
| 2008/0120372 A1* | 5/2008 | Kariathungal | G16H 30/40 709/204 |
| 2008/0189137 A1 | 8/2008 | Gentiles et al. | |
| 2009/0208118 A1* | 8/2009 | Csurka | G06V 20/10 382/228 |
| 2009/0228299 A1* | 9/2009 | Kangarloo | G16H 30/40 707/999.005 |
| 2011/0028825 A1* | 2/2011 | Douglas | G06T 19/00 600/407 |
| 2012/0183188 A1* | 7/2012 | Moriya | G16H 30/20 382/128 |
| 2012/0265557 A1 | 10/2012 | Schwalb et al. | |
| 2014/0149407 A1 | 5/2014 | Qian et al. | |
| 2014/0316770 A1* | 10/2014 | Sevenster | G16H 15/00 704/9 |

\* cited by examiner

| Report text | Extracted body part | Comments |
|---|---|---|
| CHEST:<br>........<br>MEDIASTINUM AND HILA: Stable enhancing right thyroid inferior lobe nodule, and hypoattenuating...<br><br>partially calcified right heart border reference lesion measures 2.4 x 1.6 cm (serie 11 image number 65) | heart | Mapped to Mediastinum, CT, WW/L 400/40 |
| ABDOMEN:<br>LIVER, BILIARY TRACT: The left hepatic reference lesion (serie number 11, image number 79) measures approximately 6.4 x 5.4 cm, | LIVER | Mapped to most specific body part Liver, CT, WW/L 200/50 |
| ABDOMEN:<br>........<br>BOWEL, MESENTERY: The perigastric/peripancreatic, calcified and reference lesion (series number 11, and image number 89) measures... | ABDOMEN | Most specific would be Bowel, but there is no mapping in lookup table and hence would map to Abdomen, CT, WW/L 400/40 |

AUTOMATICALLY SETTING WINDOW WIDTH/LEVEL BASED ON REFERENCED IMAGE CONTEXT IN RADIOLOGY REPORT

CROSS-REFERENCE TO PRIOR APPLICATIONS

This application is the U.S. National Phase application under 35 U.S.C. § 371 of International Application No. PCT/IB2014/066280, filed on Nov. 24, 2016, which claims the benefit of U.S. Provisional Application No. 61/908,864, filed on Nov. 26, 2013. These applications are hereby incorporated by reference herein.

BACKGROUND

Radiologists must routinely work with an increasing number of studies to diagnose and treat patients in an optimal manner. Patients, especially ones with cancers, frequently undergo imaging exams and over time accumulate many studies and reports in their medical records. Each time a new study needs to be read, the radiologist would typically open one or more prior reports to understand the status of the patient's findings and establish clinical context. Oftentimes, in the report text, the findings are associated with reference to images along with the body part or anatomy in which the finding is located. The report may include text such as, for example, "partially calcified right heart border reference lesion measures 2.4×1.6 cm (series 11 image 65)." Generally, findings on the image references are best viewed in a setting corresponding to the anatomy. According to the above example, the findings in the referenced image may best be viewed in the image setting for window width/level of the mediastinum.

When a radiologist or other user wants to look at images of a prior study to better understand the progression of a finding, the radiologist may first open the prior study, open the series of interest (e.g., series 11), navigate to the corresponding image slice (e.g., image 65), and then set the image viewing context (e.g., window width/level corresponding to the anatomy). Manually setting each image view context is a time consuming and inefficient process which may prevent users from navigating to referenced images, resulting in a possible compromise in quality.

SUMMARY OF THE INVENTION

A method for automatically setting image viewing context. The method including extracting image references and body parts associated with the image references from a report, mapping each of the body parts to an image viewing context so that image references associated are also associated with the image viewing context, receiving a user selection indicating an image to be viewed, determining whether the user selection is one of the image references associated with the image viewing context and displaying the image of the user selection.

A system for automatically setting image viewing context. The system including a memory storing a set of instructions, a processor executing the instructions which case the processor to perform operations, including extracting image references and body parts associated with the image references from a report and mapping each of the body parts to an image viewing context so that image references associated are also associated with the image viewing context, a user interface receiving a user selection indicating an image to be viewed, the processor determining whether the user selection is one of the image references associated with the image viewing context and a display displaying the image of the user selection.

BRIEF DESCRIPTION OF THE DRAWINGS

FIG. 3 shows a table of associations between image references and body parts according to an exemplary embodiment.

DETAILED DESCRIPTION

Figure 1:
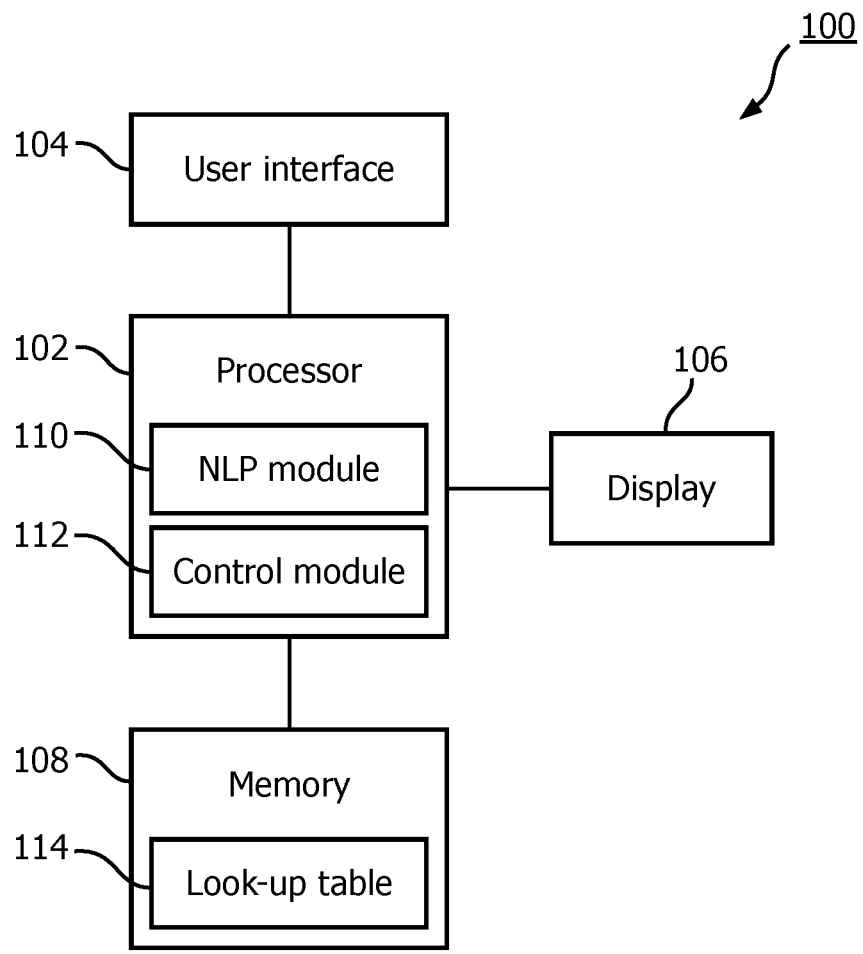
FIG. 1 shows a schematic drawing of a system according to an exemplary embodiment.

The exemplary embodiments may be further understood with reference to the following description and the appended drawings, wherein like elements are referred to with the same reference numerals. The exemplary embodiments relate to a system and method for reviewing a medical image. In particular, the exemplary embodiments describe a system and method for extracting imaging context information from free-text radiology reports and applying the imaging context information to an associated image so that a user is not required to manually set the image viewing context (e.g., a window width/level in which the associated image is to be viewed). Automatically setting image viewing context based on extracted information facilitates workflow automation and eliminates unnecessary trivial tasks currently performed by the radiologist. Although the exemplary embodiments are specifically described in regard to reviewing images of cancer patients within a radiology department, it will be understood by those of skill in the art that the system and method of the present disclosure may be utilized for patients having any of a variety of diseases or conditions within any of a variety of hospital departments.

It is noted that the exemplary embodiments are described with reference to sentences. However, those skilled in the art will understand that the same principles and functionalities described herein may be applied to text structures that have more or less context than a sentence. For example, the exemplary embodiments may be applied to a text structure that has less context such as a phrase or a text structure that has more context such as the entirety of a multi-sentence paragraph (e.g., a paragraph that is not broken into its constituent sentences).

As shown in FIG. 1, a system 100 according to an exemplary embodiment of the present disclosure extracts body part/anatomy information from a report to automatically set image viewing context for an associated image. The system 100 comprises a processor 102, a user interface 104, a display 106 and a memory 108. The processor 102 includes a Natural Language Processing (NLP) module 110 that extracts the most specific body part/anatomy surrounding an image reference in a text report of a patient stored in the memory 108. The processor 102 also includes a control module 112 which, when the user selects an image to view on the display 106, determines whether the selected image is associated with a body part/anatomy extracted by the NLP module 110. Based on the extracted image information, the processor 102 can automatically select a window width/level in which a finding (e.g., mass) in the image should be viewed. The window/width level may be selected from, for example, a look-up table 114 stored in the memory 108 which maps body parts/anatomy to window width/level settings. Thus, a user-selected image is automatically displayed on the display 106 using the window width/level settings mapped to the body part/anatomy extracted from the report in association with the selected image. It will be understood by those of skill in the art that the memory 108 may be any computer-readable storage medium. User selections may be made via the user interface 104, which may include input devices such as, for example, a keyboard, mouse and/or touch display on the display 106. It will be understood by those of skill in the art that the system 100 may be a personal computer, a server or any other known processing arrangement.

Furthermore, the exemplary system 100 relates to the display of an image and particularly, to the display of a selected image using optimal display settings (e.g., image viewing context) determined by the processor 102. These display settings can be transmitted to the display 106 and can be used to control the display operation of the system 100. It will be understood by those of skill in the art that the display 106, which displays the selected image, can be implemented in part or as a whole as a subsystem of the system 100.

Figure 2:
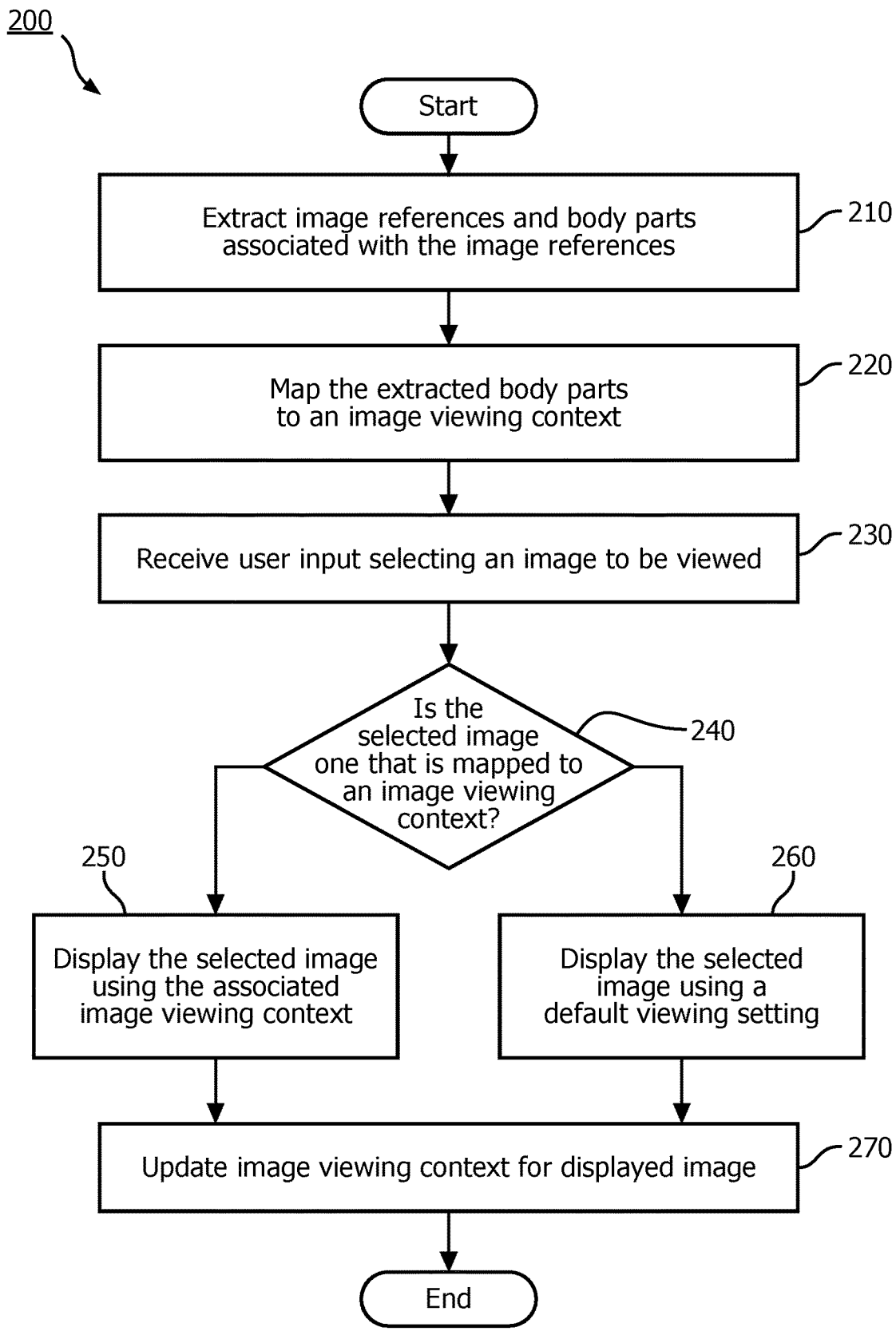
FIG. 2 shows a flow diagram of a method according to an exemplary embodiment.

FIG. 2 shows a method 200 via which the system 100 extracts image references from narrative text reports to automatically set an image viewing context (e.g., window width/level). In a step 210, the NLP module 110 extracts image references and body parts/anatomy associated with the image references from a narrative report. The NLP module 110 may analyze the report to identify sections, paragraphs and sentences therein. Once the sentences have been identified, image references may be extracted from each sentence. For example, the NLP module will extract series=11 and image=79 from the sentence "The left hepatic reference lesion (series number 11, image number 79) measure approximately 6.4×5.4 cm." The NLP module 110 may then extract the body part that the image reference refers to from a surrounding area within the report (e.g., the same sentence and/or a header of the anatomical subsection). In the above example, the NLP module 110 would recognize the term "hepatic region" and would thus associate the image reference (e.g., image 79 in series 11) to the liver.

In a step 220, the processor 102 looks up the extracted body parts in the look-up table 114 so that the extracted image reference associated with each of the extracted body parts is also associated with a corresponding image viewing context (e.g., window width/level). The look-up table 114 may also map the body parts to image viewing context based on a modality (e.g., CT, MRI, X-ray) of the image. For example, a window width/level for the same body part may be different for a CT image and an MRI image. FIG. 3 shows a table of examples of different ways in which image references may be associated with body parts and image viewing context. It will be understood by those of skill in the art that FIG. 3 is exemplary only and does not show a comprehensive list of all possible body part/image viewing context combinations. Using the above example in which image 79 in series 11 is associated with the liver, the processor 102 may look up the liver in the look-up table 114 to determine the window width/level (e.g., 200/50) to which it is mapped. Image 79 in series 11 is then associated with the window width/level 200/500 so that when this particular image is selected to be viewed, the image is automatically displayed using these display settings. The processor 102 will attempt to map the most specific body part in the look-up table 114. However, where a body part is not mapped in the look-up table 114, the processor 102 will automatically map to a more general part of the body. For example, where the NLP module 110 has extracted the bowel as the body part associated with an image reference, but the bowel is not mapped in the look-up table 114, the processor 102 will automatically look-up the body part of the abdomen, in which the liver is located. The image references and associated body parts and image viewing context may be stored to the memory 108 so that the image references and their associated content may be quickly and easily accessed.

In a step 230, the user selects an image to be viewed from the report via the user interface 104. In a step 240, control module 112 determines whether the selected image is one that is associated with an image viewing context based on the extracted body parts in step 210. For cases in which the selected image is one that is associated with corresponding image viewing context, the method 200 may proceed to a step 250 in which the selected image is displayed on the display 106 using the associated image viewing context. For example, where the user has selected image 79 in series 11 for viewing, the image is displayed using window width/level 200/50. For cases in which the selected image is not associated with corresponding image viewing context, the method 200 proceeds to a step 260 in which the selected image is displayed on the display 106 using default settings. The default setting may be, for example, predetermined window width/level values. In another example, the default setting may be determined by whether a key image has been identified in the study and setting the default image viewing context to correspond to a body part shown in the key image. A key image is an image noted by a radiologist or other user as being of particular relevance or importance within the clinical context of the patient. It will be understood by those of skill in the art that the user may adjust the default setting, as desired. It will also be understood by those of skill in the art that the default setting may automatically adjust to correspond to a body part extracted from surrounding image references within the report.

In a further embodiment, once the selected image has been displayed, the user may update the image viewing context of the displayed image, as desired, via the user interface 104. For example, the user may override the automatically set window width/level and adjust the view settings according to his/her preference. The updated image viewing context may be stored to the memory 108 so that the image reference is now associated with the updated image viewing context. It will be understood by those of skill in the art, however, that this is not a required step. Image viewing context preferences may be user-specific so that the updated image viewing context may be stored to specific user profiles.

It is noted that the claims may include reference signs/numerals in accordance with PCT Rule 6.2(b). However, the present claims should not be considered to be limited to the exemplary embodiments corresponding to the reference signs/numerals.

Those skilled in the art will understand that the above-described exemplary embodiments may be implemented in any number of manners, including, as a separate software module, as a combination of hardware and software, etc. For example the NLP module 110 and the control module 112 may be programs containing lines of code that, when compiled, may be executed on a processor.

It will be apparent to those skilled in the art that various modifications may be made to the disclosed exemplary embodiment and methods and alternatives without departing from the spirit or scope of the disclosure. Thus, it is intended that the present disclosure cover the modifications and variations provided that they come within the scope of the appended claims and their equivalents.

What is claimed is:

1. A method for automatically setting image viewing context, comprising:
mapping each of the body parts to an image viewing context so that image references associated with the body parts are associated with the image viewing context, said image viewing context including display settings for displaying an image, wherein mapping each of the body parts to an image viewing context includes:
initially mapping the one of the body parts to a generalized body part in the look-up table, and
locating each of the body parts in a look-up table which maps body parts to corresponding image viewing contexts,
wherein a first image viewing context for a body part using a first modality is different from a second image viewing context for the body part using a second modality of the image to be viewed;
receiving a user selection indicating an image to be viewed;
determining whether the user selection is one of the image references associated with the image viewing context based on the extracted image references and body parts associated with the image references from the radiology report;
displaying the image of the user selection according to a default setting when the user selection is not one of the image references associated with the image viewing context, wherein the default setting automatically adjusts to correspond to a similar body part extracted from a surrounding image reference within the radiology report;
receiving a user input updating the image; and
displaying the updated image based on a specific user profile, wherein the user profile includes an image viewing context generated based on user preferences and stored as the image viewing context for the updated image.

2. The method of claim 1, wherein extracting image references and body parts associated with the image references includes:
determining text structure boundaries to identify each text structure in the radiology report;
extracting image references from each text structure; and
extracting a body part associated with each of the image references from a surrounding text in the radiology report.

3. The method of claim 1, wherein displaying the image of the user selection includes displaying the image according to the image viewing context associated with the one of the image references, when the user selection is one of the image references associated with the image viewing context.

4. The method of claim 1, wherein the default setting is one of a predetermined image viewing context and key image viewing context mapped to a body part of an identified key image.

5. The method of claim 4, further comprising:
adjusting the predetermined image viewing context based upon a user input.

6. The method of claim 1, wherein the image viewing context is a window width/level.

7. The method of claim 1, further comprising:
receiving an updated image viewing context and displaying the image according to the updated image viewing context.

8. The method of claim 1, wherein the image references further comprise a series and image number.

9. A system for automatically setting image viewing context, comprising:
mapping each of the body parts to an image viewing context so that image references associated with the body parts are associated with the image viewing context, said image viewing context including display settings for displaying an image, wherein mapping each of the body parts to an image viewing context includes:
initially mapping the one of the body parts to a generalized body part in the look-up table, and
locating each of the body parts in a look-up table which maps body parts to corresponding image viewing contexts,
wherein a first image viewing context for a body part using a first modality is different from a second image viewing context for the body part using a second modality of the image to be viewed;
a user interface receiving a user selection indicating an image to be viewed, the processor determining whether the user selection is one of the image references associated with the image viewing context based on the extracted image references and body parts associated with the image references from the radiology report; and
a display displaying the image of the user selection according to a default setting when the user selection is not one of the image references associated with the image viewing context, wherein the default setting automatically adjusts to correspond to a similar body part extracted from a surrounding image reference within the radiology report,
wherein the user interface receives a user input updating the image, and
wherein the display displays the updated image based on a specific user profile, the user profile including an image viewing context generated based on user preferences and stored as the image viewing context for the updated image.

10. The system of claim 9, wherein the processor extracts image references and body parts associated with the image references by determining text structure boundaries to identify each text structure in the radiology report, extracting image references from each text structure and extracting a body part associated with each of the image references from a surrounding text in the radiology report.

11. The system of claim 9, wherein the display displays the image of the user selection according to the image viewing context associated with the one of the image references, when the user selection is one of the image references associated with the image viewing context.

12. A non-transitory computer-readable storage medium including a set of instructions executable by a processor, the set of instructions, when executed by the processor, causing the processor to perform operations, comprising:
mapping each of the body parts to an image viewing context so that image references associated with the body parts are associated with the image viewing context, said image viewing context including display settings for displaying an image, wherein mapping each of the body parts to an image viewing context includes:
initially mapping the one of the body parts to a generalized body part in the look-up table, and
locating each of the body parts in a look-up table which maps body parts to corresponding image viewing contexts, wherein a first image viewing context for a body part using a first modality is different from a second image viewing context for the body part using a second modality of the image to be viewed;

receiving a user selection indicating an image to be viewed;

determining whether the user selection is one of the image references associated with the image viewing context based on the extracted image references and body parts associated with the image references from the radiology report;

displaying the image of the user selection according to a default setting when the user selection is not one of the image references associated with the image viewing context, wherein the default setting automatically adjusts to correspond to a similar body part extracted from a surrounding image reference within the radiology report;

receiving a user input updating the image; and displaying the updated image based on a specific user profile, wherein the user profile includes an image viewing context generated based on user preferences and stored as the image viewing context for the updated image.

* * * * *